United States Patent [19]

Oppelt et al.

[11] 4,066,614
[45] Jan. 3, 1978

[54] HETEROCYCLICAMIDES OF HINDERED 3,5-DIALKYL-4-HYDROXYBENZOIC ACIDS AND USE AS LIGHT STABILIZERS IN POLYOLEFINS

[75] Inventors: John Christian Oppelt, Somerville; Peter Vincent Susi, Middlesex, both of N.J.

[73] Assignee: American Cyanamid Company, Stamford, Conn.

[21] Appl. No.: 537,154

[22] Filed: Dec. 30, 1974

[51] Int. Cl.² .................. C07D 295/18; C08K 5/34; C08K 5/35; C08K 5/47
[52] U.S. Cl. .................. 260/45.8 NZ; 260/45.8 N; 260/45.8 SN; 260/268 C; 260/293.77; 260/306.7 R; 260/326.5 E; 544/173
[58] Field of Search ............. 260/45.8 NZ, 247.7 V, 260/45.8 N, 45.8 SN, 293.77, 306.7 R, 326.5 E

[56] References Cited
U.S. PATENT DOCUMENTS

| 2,906,728 | 9/1959 | Schweitzer | 260/45.8 |
| 3,022,302 | 2/1962 | Martensson | 260/247.7 |
| 3,282,939 | 11/1966 | Spivack et al. | 260/247.7 |
| 3,330,859 | 7/1967 | Dexter et al. | 260/473 |
| 3,449,419 | 6/1969 | Wechter | 260/559 |
| 3,573,304 | 3/1971 | Eberle | 260/250 |

OTHER PUBLICATIONS

Noller, "Chemistry of Organic Compounds", 1957, pp. 160, 249 and 252.

Primary Examiner—Donald E. Czaja
Assistant Examiner—R. A. White
Attorney, Agent, or Firm—Philip Mintz; Frank M. Van Riet

[57] ABSTRACT

Compounds of the formula:

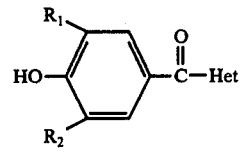

wherein $R_1$ and $R_2$ are each branch-chain alkyl of 3 to 8 carbon atoms and -Het is a nitrogen-containing heterocyclic moiety attached to the carbonyl carbon atom through a heterocyclic nitrogen are useful as light stabilizers in polyolefins. They may be prepared (a) by reacting the 3,5-dialkyl-4-hydroxybenzoyl chloride with the appropriate heterocyclic amine in the presence of an acid acceptor or (b) by reacting the corresponding benzoic acid with the appropriate heterocyclic amine in the presence of a carbodiimide as dehydrating agent.

10 Claims, No Drawings

HETEROCYCLICAMIDES OF HINDERED 3,5-DIALKYL-4-HYDROXYBENZOIC ACIDS AND USE AS LIGHT STABILIZERS IN POLYOLEFINS

This invention relates to stabilizing polyolefins against the deteriorating effects of light by the use of certain amides of 3,5-dialkyl-4-hydroxybenzoic acid.

As is well known, polyolefins such as polypropylene and polyethylene tend to deteriorate from the effects of light, especially ultraviolet light. This deterioration generally manifests itself as a loss of tensile strength and loss of flexibility of the polymer. In accordance with the present invention, we have discovered that certain amides of 3,5-dialkyl-4-hydroxybenzoic acid can significantly retard or inhibit such deterioration.

The amides of 3,5-dialkyl-4-hydroxybenzoic acid useful for the practice of the present invention include those having the formula:

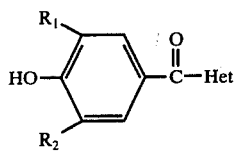

wherein $R_1$ and $R_2$ are each branched-chain alkyl of 3 to 8 carbon atoms and Het is a nitrogen-containing heterocyclic moiety attached to the carbonyl carbon atom through a heterocyclic nitrogen. Illustrative of the branched-chain alkyl moieties from which $R_1$ and $R_2$ may be separately selected are isopropyl, t-butyl, isohexyl, cyclohexyl, 2-ethylhexyl, t-octyl, etc. It is preferred for both $R_1$ and $R_2$ to be t-butyl because of the commercial availability of 3,5-di-t-butyl-4-hydroxybenzoic acid, an intermediate from which the amides of the present invention can be prepared. Illustrative of the heterocyclic moieties from which -Het can be selected are those obtained after removal of the hydrogen attached to the heterocyclic nitrogen of morpholine, piperidine, pyrrolidine, 3-pyrroline, thiazolidine, N-methylpiperazine, 4-methylpiperidine, etc. Preferably, -Het is -morpholino.

These new compounds can be prepared in several ways from 3,5-dialkyl-4-hydroxybenzoic acid or its acid chloride. Briefly, one such preparation involves the reaction of the acid chloride with the appropriate amine in the presence of an acid acceptor. Another such preparation involves the condensation of the acid with the appropriate amine in the presence of a carbodiimide as dehydrating agent.

The 3,5-dialkyl-4-hydroxybenzoic acid chloride can be prepared by reacting the corresponding benzoic acid with thionyl chloride in the presence of a catalyst, such as pyridine. The benzoic acid may be purchased (especially the 3,5-di-t-butyl-4-hydroxybenzoic acid) or may be prepared by oxidation of the corresponding aldehyde; see Yohe et al., J. Org. Chem., 1289 (1956) as explained in U.S. Pat. No. 3,206,431 col. 3, lines 32-35. The acid and acid chloride are also described in U.S. Pat. No. 3,330,859 (Examples 3, 5, and 6).

The compounds of this invention are useful for protecting polyolefins, such as polypropylene and polyethylene, against the deteriorating effects of ultraviolet light when used in amounts of about 0.1 to about 2.0 percent by weight, preferably of about 0.2 to about 1.0 percent by weight, on weight of polymer. These compounds may be incorporated into the polyolefin by any of the standard techniques used in industry, such as by milling, extrusion, swelling into the polymer, etc. Other additives, such as processing antioxidants, secondary stabilizers, pigments, dyes, flame retardants, lubricants, plasticizers, etc. may also be included in the polyolefin for their usual purposes.

For further illustration of this invention, reference should be made to the following examples.

EXAMPLE 1

To a stirred solution of 25 grams (0.1 mole) of 3,5-di-t-butyl-4-hydroxybenzoic acid and 8.7 grams (0.1 mole) of morpholine in 100 milliliters of dry tetrahydrofuran was added dropwise a solution of 20.6 grams (0.1 mole) of dicyclohexylcarbodiimide in 75 milliliters of dry tetrahydrofuran. The mixture was stirred for several hours and the white solid (dicyclohexyl urea) was filtered off and discarded. Evaporation of the filtrate gave a white solid, which was recrystallized from 1:1 benzene-hexane to give 24 grams of 3,5-di-t-butyl-4-hydroxybenzomorpholide; melting point 125°–127° C.

EXAMPLE 2

Testing in Polypropylene

The compound of Example 1 (0.5% by weight) was milled into unstabilized polypropylene along with 0.2% by weight of a thermal antioxidant, 2,4,6-tri-t-butylphenol. The milled composition was then compression molded into a film 4 mils thick. The compression molded film, and a control film identically prepared except without the compound of Example 1, were exposed in a Fade-Ometer until they failed. The samples were considered as having failed when the carbonyl content in the film, as measured in the infra-red specturm, reached 0.1%. This carbonyl content generally results in film embrittlement. The test sample lasted 1150 hours, about 3.8 times as long as the control.

In a manner similar to Example 1, 3,5-di-t-butyl-4-hydroxybenzoic acid can be reacted with piperidine, pyrrolidine, 3-pyrroline, thiazolidine, N-methylpiperazine, or 4-methylpiperidine to give the appropriate amides of this acid.

What is claimed is:

1. A compound of the formula:

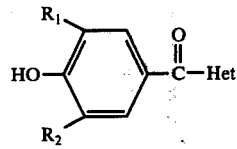

wherein $R_1$ and $R_2$ are each branch-chain alkyl of 3 to 8 carbon atoms and -Het is a nitrogen-containing heterocyclic moiety attached to the carbonyl carbon atom through a heterocyclic nitrogen.

2. A compound as defined in claim 1 wherein $R_1$ and $R_2$ are each t-butyl.

3. A compound as defined in claim 1 wherein -Het is -morpholino.

4. A compound as defined in claim 3 wherein $R_1$ and $R_2$ are each t-butyl.

5. A polyolefin stabilized against the deteriorating effects of light by having incorporated therein an effective amount of a light stabilizer of the formula:

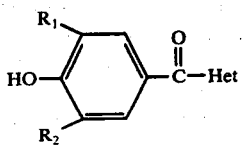

wherein $R_1$ and $R_2$ are each branch-chain alkyl of 3 to 8 carbon atoms and -Het is a nitrogen-containing heterocyclic moiety attached to the carbonyl carbon atom through a heterocyclic nitrogen.

6. A composition as defined in claim 5 wherein $R_1$ and $R_2$ are each t-butyl.

7. A composition as defined in claim 5 wherein -Het is -morpholino.

8. A composition as defined in claim 7 wherein $R_1$ and $R_2$ are each t-butyl.

9. A composition as defined in claim 5 wherein said polyolefin is polypropylene.

10. A composition as defined in claim 8 wherein said polyolefin is polypropylene.

* * * * *